United States Patent [19]

Kumar

[11] Patent Number: 4,599,403

[45] Date of Patent: Jul. 8, 1986

[54] METHOD FOR RECOVERY OF STEVIOSIDE

[75] Inventor: Sampath Kumar, Lincroft, N.J.

[73] Assignees: Harold Levy; Harry W. Sorkin; Edna Y. Rogers, all of New York, N.Y.; Charles F. Bruno, East Brunswick, N.J.

[21] Appl. No.: 785,200

[22] Filed: Oct. 7, 1985

[51] Int. Cl.⁴ ............................................. C07H 1/08
[52] U.S. Cl. ................................. 536/18.1; 536/18.5; 536/128
[58] Field of Search ...................... 536/18.1, 18.5, 128

[56] References Cited

U.S. PATENT DOCUMENTS 4,171,430 10/1979 Matsushita et al. ................ 536/18.1
4,454,290 6/1984 DuBois ............................... 536/18.1

*Primary Examiner*—Johnnie R. Brown
*Attorney, Agent, or Firm*—Lawrence Rosen

[57] ABSTRACT

An improved method for the recovery of stevioside from *Stevia rebaudiana* Bertoni plants is provided which does not require the use of dangerous chemicals or special separation equipment such as ion exchange or chromatography. In the process the raw material, preferably in comminuted form is first extracted with water, the resulting aqueous extract is treated with a di- or tricarboxylic acid chelating agent to remove metallic and other impurities as well as to lower the pH to less than about 4. Subsequently a calcium-containing agent is added to precipitate out other impurities. The aqueous extract is essentially neutralized with an acid and is then subject to extraction with a water-immiscible solvent. Purified stevioside crystals are recovered by cooling the water layer obtained from said solvent extraction step.

17 Claims, No Drawings 4,599,403

METHOD FOR RECOVERY OF STEVIOSIDE

BACKGROUND OF THE INVENTION

1. Field of the Invention

The present invention is concerned with the recovery of stevioside from the Stevia rebaudiana Bert. Hemsl. (Compositae), hereinafter referred to as *Stevia rebaudiana*. More particularly, the invention pertains to an improved method for recovery of stevioside from the Stevia rebaudiana plant without the need to use chemicals that might in turn end up as undesirable impurities in the stevioside product or which require the use of equipment that render commercial operations uneconomic.

Stevioside of a natural origin is gaining favor as a low calorie or nutritive sweetener. It has been used commercially in Japan for many years and recently in Brazil to sweeten a variety of foods. The present investigation was undertaken in order to find a commercially viable method for the isolation of purified stevioside, since it is present only to an extent of 8–10% in the *Stevia rebaudiana* leaves.

Stevioside is one of the eight known sweet ent-kaurene glycoside constituents of *Stevia rebaudiana;* the others being Steviolbioside, rebaudicides A-E, and dulcoside-A. Stevioside possesses the empirical formula $C_{36}H_{60}O_{18}$ and the following structural formula:

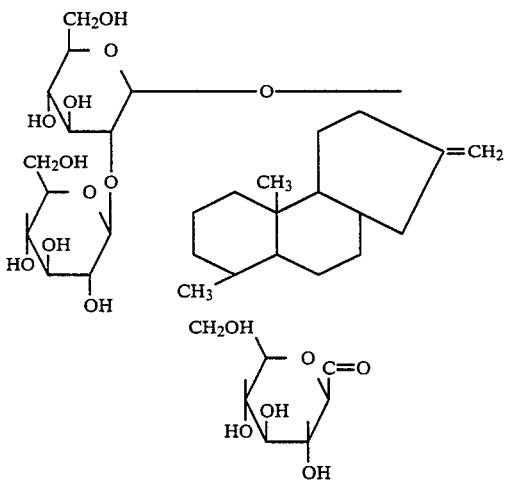

2. Description of the Prior Art

U.S. Pat. No. 4,361,697 which issued on Nov. 30, 1982 to Dobberstein and Ahmed discloses a process for the recovery of diterpene glycosides, including stevioside from the *Stevia rebaudiana* plant. A variety of solvents, having different polarities, were used in a sequential treatment that concluded with a high performance liquid chromatographic (HPLC) separation procedure.

Dobberstein and Ahmed called attention to U.S. Pat. No. 4,082,858 which issued on Apr. 4, 1979 to Morita et al. This earlier patent is directed to the recovery of rebaudside A from the leaves of *Stevia rebaudiana* plants. Again, final purification is achieved by liquid chromatography subsequent followed by an initial extraction with water an alkanol having from 1 to 3 carbon carbons, preferably methanol. Although Dobberstein and Ahmed also disclose that water may be used as the initial solvent, their preferred solvent at this stage is a liquid haloalkane having from 1 to 4 carbon atoms. The preferred second solvent is an alkanol having from 1 to 3 carbon atoms, while the preferred third solvent is an alkanol having from 1 to 4 carbon atoms and optionally minor amounts of water.

In addition to Morrita et al. the Dobberstein and Ahmed patent shows the following list of cited U.S. patent references:

U.S. Pat. No. 3,723,410, Persinos
U.S. Pat. No. 4,109,075, Deaton
U.S. Pat. No. 4,171,430, Matsushita et al.
U.S. Pat. No. 4,256,876, Gabriel et al.

Publications cited include two articles by Y. Hashiomoto et al. and one article by M. S. Ahmed et al.

There are also numerous published Japanese patent applications, only abstracts of which are available, which deal with the separation of steviocide from naturally occurring sources. Some of the more relevant Japanese patents with respect to the present invention are set forth below:

| | | |
|---|---|---|
| Toyo Sugar Refining | 57198 | May 1977 |
| Chigai Pharmaceutical | 51069 | April 1977 |
| Ajinomoto | 62300 | May 1977 |
| Sanei Chem. Ind. | 148574 | Dec. 1978 |
| Sanei Chem. Ind. | 148575 | Dec. 1978 |
| Sanyo Kokusaku Pulp | 132599 | Oct. 1979 |
| Teijin Eng. | 21752 | Feb. 1980 |
| Seisan Kaihatsu | 39731 | March 1980 |
| Seisan Kaihatsu | 81567 | June 1980 |
| Oshiro Chiyi Sholten | 92323 | July 1980 |
| Ajinomoto | 121454 | Sept. 1981 |
| Dick Fine Chem. | 160962 | Dec. 1981 |
| Maruzen Kasei | 86264 | May 1982 |
| Shin-Nakamura | 42300 | Sept. 1982 |
| Matsubishi Acetate | 28247 | Feb. 1983 |
| Sekisui Chem. Ind. | 212759 | Dec. 1983 |

It is abundantly clear from the above patent literature that there have been numerous proposals for the recovery and separation of stevioside from *Stevia rebaudiana* plants. The proposals have included treatments such as ion-exchange, column chromatography, multiple solvent extractions, etc. In many of these processes undesirable chemicals have to be employed or the equipment required is too expensive for practical commercial operations.

It is therefore a principal object of the present invention to provide an improved method for the treatment of *Stevia rebaudiana* plants to recover purified stevioside therefrom utilizing innocuous chemicals in the separation procedures; while eliminating the need for large volumes of solvents as well as the use of expensive ion exchange resins, chromatographic equipment, and the like.

SUMMARY OF THE INVENTION

In accordance with the present invention a initary method has been developed for the recovery of purified stevioside from naturally occurring *Stevia rebaudiana*. The method utilizes a series of steps which successively removes impurities as well as undesirable components for the present purposes. The materials employed to effect such separation are harmless and in some instances can readily be recovered and recycled thereby achieving desirable economies. Moreover, the present invention avoids the use of expensive and time-consuming procedures and equipment such as ion exchange and chromatography, which are characteristic of the most recently proposed processes for the treatment of *Stevia rebaudiana* plants.

More particularly, the present invention comprises treating comminuted *Stevia rebaudiana* leaves with hot water to isolate the glycosides therefrom. The pH of the aqueous extract is then lowered to less than about 4 pH by addition of an organic carboxylic acid capable of chelating metals, protein and color-imparting impurities. The pH of the separated aqueous extract is next raised to at least 10 pH by addition of a base and filtered. The aqueous filtrate is essentially neutralized and subsequently extracted with a water-immiscible alkanol having from 4 to 6 carbon atoms. The solvent layer is concentrated, and stevioside crystallized therefrom by temperatures below about 15° C. In some instances the stevioside crystals may be dissolved in a lower alkanol having from 1 to 4 carbon atoms, preferably methanol or ethanol. By practicing the above described method highly purified stevioside has been recovered.

DETAILED DESCRIPTION OF THE INVENTION

The *Stevia rebaudiana* plants, and generally the leaves of these plants, are comminuted to provide the starting material for the method of this invention. Conventional grinding or milling procedures may be used to provide finely divided *Stevia rebaudiana* having a mesh size that may range from about 50 to 400, preferably 100-300 mesh.

Initially the finely divided *Stevia rebaudiana* is contacted with hot water at a temperature of from about 50° to 95° C., preferably 60° to 80° C., for a time period sufficient to extract substantially all of the glycosides from the starting material. In general the extraction will take about 2 to 5 hours.

The aqueous extract is ordinarily concentrated 25 to 75% of its volume to remove excess water and thereby reduce the amount of material being subsequently treated. It should be understood that although this concentration procedure as well as other concentration treatments, are not critical features of the present invention and consequently must be viewed as optional expedients, there are many obvious commercial advantages to reducing the volumes of materials being treated. The equipment used for concentration will be conventional, e.g. rotary evaporators, and operated under the usual and non-critical conditions.

The second major step comprises reducing the pH of the aqueous extract to less than about pH 4, and preferably about pH 2 to 4. It is a feature of the present invention to organic dicarboxylic or tricarboxylic acids that will also function as chelating agents to remove metallic, protein, and color-imparting impurities. Although citric acid is especially preferred for the purpose, other carboxylic acids such as fumaric and tartaric may be employed. Other chelating agents such as the salts of trivalent metals such as alumina, ferric chloride, aluminum chloride, certain Lewis acids, ethylene diamine tetraacetic acid (EDTA), sodium glucono-delta-lactone, and carbon dioxide gas, these latter agents do not give the impurity removal results achieved with citric acid. It was further noted that fumaric and tartaric acids, gave somewhat better results, but the purification was still not as good as when citric acid was utilized. Mineral acids, with the possible exception of phosphoric acid, were ineffective.

Following addition of the chelating agent it has been found advantageous to vigorously stir or agitate the aqueous extract at temperatures of from about 30° to 80° C. for about from about 1 to 2 hours or longer. Higher temperatures should be avoided since in the presence of acids they tend to hydrolyze the glycosidic bonds.

The thus treated aqueous extracted mixture is filtered. Filtration through diatomaceous earth, e.g. such as that sold under the trademark Celite has been found to be especially efficient for this and other filtrations carried out in the practice of the present invention.

The aqueous filtrate, having a pH of 2 to 4, is then treated with a base to raise the pH to about 10 to 13. The base is preferably calcium oxide or calcium hydroxide (slaked lime). Although magnesium hydroxide or potassium aluminum sulfate (alum) in a dilute sodium solution may also be utilized. The base treated solution is then generally heated between 35° to 80° C., preferably from 50° to 60° C., for about 1 to 2 hours, cooled to ambient temperature with slow or mild agitation, and finally filtered through diatomaceous earch to remove solids comprising certain proteins, plant pigments, etc.

The resulting filtrate, having a pH from about 10 to 12 and almost colorless, is essentially neutralized with an di- or tricarboxylic acid such as citric, tartaric, fumaric acids. The preferred organic acid for this purpose is again citric acid, although a mineral acid such as phosphoric acid, alum or glucono-delta-lactone may be used for this purpose.

The almost colorless, essentially neutralized filtrate is next treated with about an equal volume of a water-immiscible, organic solvent. Especially preferred are alkanol solvents having from 4 to 6 carbon atoms, and the most preferred solvent is n-butanol. The solvent layer is separated while the aqueous layer is preferably concentrated to 25 to 50% or less of its original volume.

The concentrated aqueous layer is then cooled to a temperature below the crystallization temperature of stevioside for about 10 to 24 hours, preferably from about 8 to 14 hours. Temperatures below about 15° C., and preferably from about 5° to 12° C., are sufficient for this purpose. Colorless crystals of stevioside separate out and are removed by filtration and dried.

In the event that, upon examination it appears that some calcium salts may be present, they are readily removed by dissolving the stevioside crystals in a boiling lower alkanol having 1 to 3 carbons, especially methanol or ethanol. After filtration, the temperature of the filtrate is again lowered to below the crystallization temperature of stevioside. Highly purified stevioside is obtained.

The stevioside crystals may be used as such or in formulation as sweeteners for various foodstuffs, carbonated and non-carbonated beverages, pharmaceuticals, chewing gums, tobacco, cosmetics, toothpastes, mouthwashes, and the like.

For the purposes of illustration only, the invention will be described below in connection with certain embodiments as well as the best mode contemplated for carrying out the invention. However, it will be understood that various changes and modifications in the method may be made without departing from the spirit and scope of the invention as described and claimed herein.

EXAMPLE 1

1.0 kg of finely divided leaves of *Stevia rebaudiana* were extracted with 5 liters of hot water at 75° C. for four hours. The leaves which are sweet before extraction did not taste sweet after extraction, and thin layer chromatography of the extract showed four spots corresponding to stevioside and other diterpenoid glycosides. The water extract was concentrated to about 2 liters in a rotary evaporator. The pH of this concentrate was adjusted to 3.0 with 50% citric acid and stirred constantly for 30 minutes, cooled to ambient temperature and filtered through Celite. The filtrate was heated to 50°–55° C. on a water bath and the pH raised to 10.5 with the addition of solid calcium oxide. It was kept agitated at the same temperature (50°–55° C.) for 60 minutes. It was cooled to ambient temperature with slow agitation, and the precipitated salts of calcium filtered off on a Celite pad. The clear yellow solution now at pH 9.5 was adjusted to a pH of about 7.1 with 10% citric acid and concentrated on a rotary evaporator to about 250 ml. The syrupy mass was triturated with n-butanol when the light yellow color separated into butanol layer (upper level). It was separated, the lower aqueous layer cooled to 0°–5° C. overnight to crystallize. The crystals formed were removed by filtration. The crystals were dried under vacuum at 80°–90° C. and weighed. The yield was 75 gms (7.5%) of stevioside. Thin layer chromatography (TLC) examination (Butanol:acetic acid:water 4:1:1 solvent system) revealed the presence of only one spot corresponding to stevioside on spraying with orcinol reagent.

EXAMPLE 2

500 gms of air-dried, finely powdered leaves of *Stevia rebaudiana* Bertoni (compositae) was extracted with hot water for three hours at 70°–75° C. The extract concentrated, and pH adjusted to 4.0 with tartaric acid and heated to 50°–55° C., cooled to ambient temperature and filtered through Celite.

The filtrate was clear with a yellowish green color. It was reheated to 60° C. and the pH adjusted to 11.0 with solid calcium oxide. After standing for one hour with mild agitation, it was filtered through Celite and the pH adjusted to 7.0 with dilute phosphoric acid. The solution was almost colorless at this stage. It was concentrated to about 100 ml and the remaining colored bodies removed by extracting with n-butanol. The aqueous layer crystallized to yield 35 gms of stevioside. On drying, the sample melted at 196°–98° C. and showed one spot on TLC.

EXAMPLE 3

225 gms of finely powdered leaves of *Stevia rebaudiana* was extracted with hot water (1 liter) for two hours at 70° C. The extract was filtered through Whatman #1 filter paper and the clear green solution (800 ml) was concentrated to 400 ml on a rotary evaporator at 60° C. and 20 mm pressure. The pH of this concentrate was brought down to pH 3.5 with fumaric acid. It was refiltered and the pH of the filtrate adjusted to 10.0 with dilute sodium hydroxide. A pasty mass separated out. It was filtered and the pH of the filtrate readjusted 8.5 with the addition of potassium aluminum sulfate (alum). The solution was clear and completely clarified. It was let stand for several hours and distilled by using n-butanol as azeotrope. The concentrate was recrystallized from methanol to yeild 20 gms of pure stevioside, identified by m.p. mixed m.p. and TLC.

EXAMPLE 4

This Example was similar to Example 3, but the pH of the extract adjusted to 11.5 with calcium oxide filtered and the pH of the filtrate adjusted to 6.5 with glucono-delta-lactone. After refiltereng, it was concentrated and azeotroped with n-butanol. The solids obtained after recrystallization were still green in color. TLC examination showed the presence of mostly stevioside and small amounts of impurities.

The above data show that the method of this invention is efficacious in recovering steviocide from *Stevia rebaudiana* without encountering the disadvantages of many recently proposed recovery processes. The data further show that the stevioside product of Example 1 is superior to the products of Examples 2 through 4.

What is claimed is:

1. A method for the recovery of stevioside from leaves of *Stevia rebaudiana* Bertoni which comprises the following sequential steps:
    (a) contacting said leaves with hot water to obtain an aqueous extract containing stevioside;
    (b) admixing said aqueous extract with a chelating agent whereby the pH of the aqueous extract is lowered to less than about pH 4 and metallic impurities are chelated and then separated from the aqueous extract;
    (c) contacting the thus treated aqueous extract with a base to precipitate salts of the chelating agent, protein impurities and colored impurities, and separating said precipitates from the aqueous extract;
    (d) treating the resulting aqueous extract, having a basic pH, with an acid essentially to neutralize the aqueous extract;
    (e) contacting the neutralized aqueous extract with a water-immiscible, organic solvent, and separating the resulting solvent layer from the aqueous layer;
    (f) cooling the aqueous layer to a temperature sufficient to crystallize stevioside therefrom; and
    (g) separating stevioside crystals from the cooled aqueous layer.

2. The method of claim 1 wherein in step (a) the hot water has a temperature within the range of about 75° to 90° C.

3. The method of claim 1 wherein sufficient chelating agent is added to the aqueous extract to give a pH of from about 2 to 4.

4. The method of claim 1 wherein the chelating agent is selected from the group consisting of citric acid, tartaric acid, and fumaric acid.

5. The method of claim 4 wherein the chelating agent is citric acid.

6. The method of claim 1 wherein the base is selected from the group consisting of calcium oxide, calcium hydroxide, magnesium oxide, and potassium aluminum sulfate.

7. The method of claim 6 wherein the base is calcium oxide.

8. The method of claim 1 wherein the aqueous extract, following treatment with the base, has a pH ranging from about 10 to 13.

9. The method of claim 1 wherein the aqueous extract obtained from step (c) is essentially neutralized with an organic tricarboxylic acid.

10. The method of claim 9 wherein the organic tricarboxylic acid is citric acid.

11. The method of claim 1 wherein the water-immiscible, organic solvent is an aliphatic alcohol having from 3 to 5 carbon atoms and acetate esters thereof.

12. The method of claim 11 wherein the water-immiscible, organic solvent is n-butanol.

13. The method of claim 1 wherein the stevioside crystals obtained from step (g) is recrystallized.

14. The method of claim 1 wherein the aqueous extract obtained from step (a) is heated to effect concentration.

15. The method of claim 1 wherein the aqueous layer obtained from step (e) was heated to effect concentration.

16. A method for recovery of stevioside from finely divided leaves of *Stevia rebaudiana* plants which comprises the following sequential steps:
  (a) contacting the finely divided leaves with hot water to obtain an aqueous extract which is concentrated to at least about 75% of its volume;
  (b) admixing said concentrated aqueous extract with citric acid to lower the pH to less than about 4 and to chelate metallic impurities, and separating resulting solids from the aqueous extract;
  (c) contacting the thus treated aqueous extract with a calcium-containing base to precipitate salts of the citric acid, protein, and color-impurities, and separating the precipitates from the aqueous extract;
  (d) treating the resulting aqueous extract having a pH of from about 10 to 13 with citric acid essentially to neutralize the aqueous extracts,
  (e) contacting the essentially neutralized aqueous extract with n-butanol, recovering the resulting aqueous layer and heating it to effect concentration to less than about 50% of its volume;
  (f) cooling the concentrated aqueous layer to a temperature below about 15° C. to crystallize stevioside therefrom; and
  (g) separating stevioside crystal from the cooled concentrated aqueous layer.

17. The method of claim 16 wherein the calcium-containing base is calcium oxide.

* * * * *